United States Patent [19]

McCombs

[11] Patent Number: 4,945,178

[45] Date of Patent: Jul. 31, 1990

[54] PREPARATION OF 4-CARBOALKOXY-1,3-CYCLOHEXANEDIONE TYPE COMPOUNDS

[75] Inventor: Charles A. McCombs, Kingsport, Tenn.

[73] Assignee: Eastman Kodak Company, Rochester, N.Y.

[21] Appl. No.: 314,994

[22] Filed: Feb. 24, 1989

Related U.S. Application Data

[63] Continuation of Ser. No. 825,010, Feb. 3, 1986, abandoned.

[51] Int. Cl.[5] ............................................. C07C 67/347
[52] U.S. Cl. .................................... 560/125; 544/283; 544/335; 544/336; 544/353; 546/147; 546/174; 546/342; 548/180; 548/204; 548/217; 548/236; 549/32; 549/79; 549/471; 549/501; 560/18; 560/118; 560/126
[58] Field of Search ................. 560/125, 126, 18, 118; 549/32, 79, 471, 501; 548/180, 204, 217, 236; 546/147, 174, 342; 544/283, 335, 336, 353

[56] References Cited

U.S. PATENT DOCUMENTS

| | | | |
|---|---|---|---|
| 3,737,442 | 6/1973 | Baum | 560/152 |
| 3,758,549 | 9/1973 | Dexter | 560/152 |
| 3,865,884 | 2/1975 | Agusto | 560/126 |
| 3,997,590 | 12/1976 | Lester | 560/126 |

FOREIGN PATENT DOCUMENTS

| | | |
|---|---|---|
| 124041 | 11/1984 | European Pat. Off. . |
| 142741 | 5/1985 | European Pat. Off. . |
| 2090246 | 7/1982 | United Kingdom . |

*Primary Examiner*—Michael L. Shippen
*Attorney, Agent, or Firm*—J. Frederick Thomsen; S. E. Reiter; William P. Heath, Jr.

[57] ABSTRACT

Acetoacetic esters of the formula R—OOCCH$_2$COCH$_3$ are reacted with an unsaturated ester of the formula R$^1$R$^2$C=CHCOOR$^3$ in the presence of basic catalyst such as ethanolic sodium ethoxide to give compound I of the formula

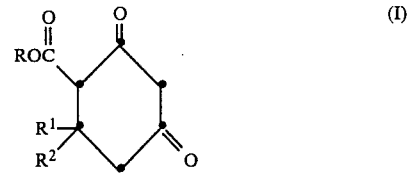

and the alcohol by-product HOR$^3$. By known hydrolysis and decarboxylation procedures, compound I is convertible to compound II of the formula

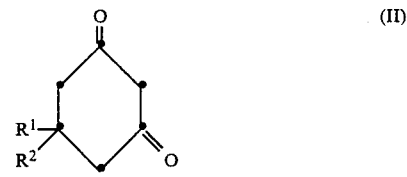

In the above formulas, R is alkyl, R$^1$ and R$^2$ are each selected independently from H, alkyl, alkylthioalkyl, cycloalkyl, alkyl substituted cycloalkyl, aryl, substituted aryl, heterocyclic, or substituted heterocyclic, and R$^3$ is alkyl or cycloalkyl. These compounds I and II are intermediates in the preparation of known herbicides.

5 Claims, No Drawings

PREPARATION OF 4-CARBOALKOXY-1,3-CYCLOHEXANEDIONE TYPE COMPOUNDS

This is a continuation of application Ser. No. 825,010 filed on Feb. 3, 1986, now abandoned.

DESCRIPTION

This invention concerns a novel and markedly improved process for the preparation of 4-carboalkoxy-1,3-cyclohexanedione type compounds. The process is especially characterized by improved yields.

The invention more particularly concerns the preparation of certain 4-carboalkoxy-5-[2-(alkylthio)-alkyl]-1,3-cyclohexanedione compounds which are useful as intermediates in the preparation of herbicides according to and such as those disclosed in U.K. Patent 2,090,246, incorporated herein by reference.

In accordance with the present invention, an acetoacetic ester of the formula $R-OOCCH_2COCH_3$ is reacted with an unsaturated ester of the formula $R^1R^2C=CHCOOR^3$ in the presence of basic catalyst such as the highly preferred ethanolic sodium ethoxide catalyst to give a compound (I) of the formula

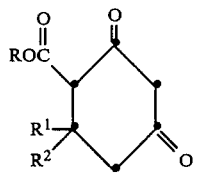

and the alcohol by-product $HOR^3$. By known hydrolysis and decarboxylation procedures, compound (I) is convertible to compound (II) of the formula

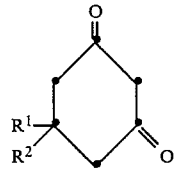

The useful basic catalysts include the groups IA and IIA metal alkoxides of $C_1-C_6$ aliphatic alcohols, or the hydroxides of these metals. In the above formulas: R is alkyl of 1-6 carbons; $R^1$ and $R^2$ are each selected independently from H, alkyl, alkylthioalkyl, cycloalkyl, alkyl substituted cycloalkyl, aryl, substituted aryl, heterocyclic, or substituted heterocyclic, wherein the alkyl groups or moieties are 1-18 carbons, preferably 1-6 carbons; and $R^3$ is alkyl of 1-6 carbons or cycloalkyl.

In the cyclization step of the present process, the preferred molar ratio of basic catalyst to total moles of reactants is from about 0.10 to about 10.0, most preferably from about 1 to about 4, the molar ratio of acetoacetic ester to unsaturated ester is from about 0.8 to about 1.5, preferably from about 1.0 to about 1.1, the weight ratio of total reactants to the $C_1-C_6$ alcohol is from about 0.01 to about 1.2, preferably from about 0.08 to about 1.0, the reaction temperature is from about 22° C. to about 88° C., preferably from about 70° C. to about 78° C., and the reaction period preferably is from about 5 to about 36, and most preferably from about 10 to about 24 hours.

The following table gives specific examples of the above R, $R^1$, $R^2$, and $R^3$ substituents. In the table each X substituent is in any ring position and is selected independently from H, alkyl of 1-6 carbons, alkoxy or 1-6 carbons, and halogen.

TABLE

| $R^3$ | R |
|---|---|
| $CH_3$ | $CH_3$ |
| $C_2H_5$ | $C_2H_5$ |
| $C_3H_7$ | $C_3H_7$ |
| $C_4H_9$ | $C_4H_9$ |
| $C_5H_{11}$ | $C_5H_{11}$ |
| $C_6H_{13}$ | $C_6H_{13}$ |
| $C_6H_{11}$ | |

| $R^1$ or $R^2$ |
|---|
| $-H, -CH_3, -C_2H_5, -C_4H_9, -C_6H_{13},$ $-C_8H_{17}, -C_{10}H_{21}, -(CH_2)_{17}CH_3,$ |

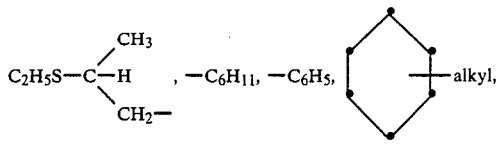

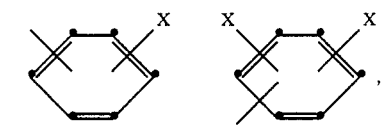

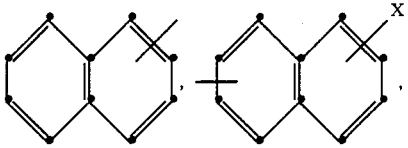

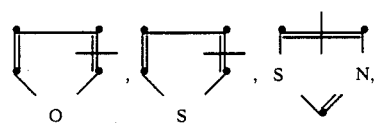

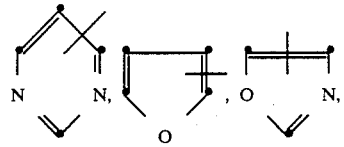

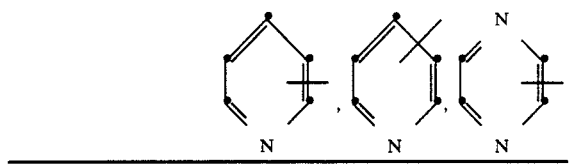

or any of the above heterocyclic structures wherein two adjacent H's are replaced with

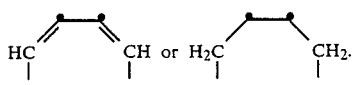

In a specific embodiment, the present process is employed to make 5-[2-(ethylthio)-propyl]-1,3-cyclohexanedione of the formula

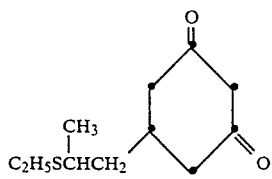

which is an intermediate in the preparation of the herbicide of the formula

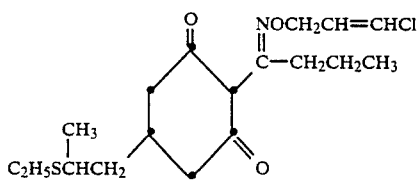

sold under the tradename SELECTONE. This herbicide is prepared from the said intermediate by the reaction sequence

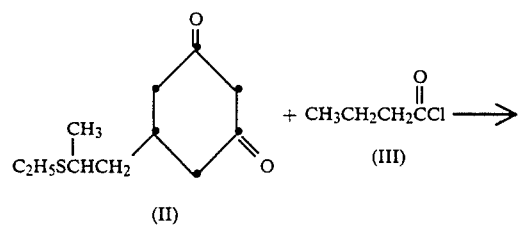

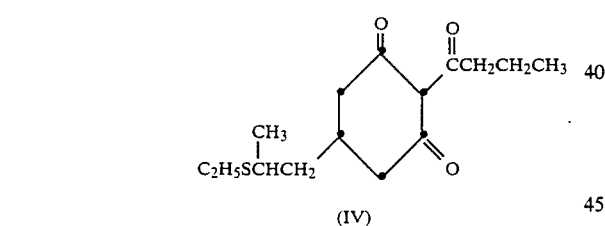

IV + H₂NOCH₂CH=CHCl ⟶

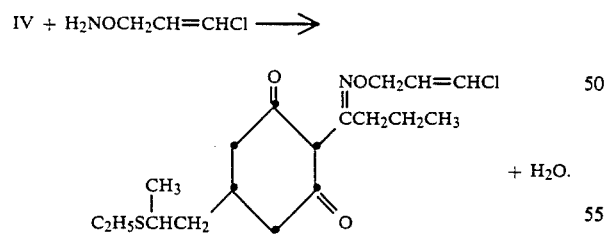

A reported route to the aforesaid intermediate 5-[2-(ethylthio)-propyl]-1,3-cyclohexanedione (I) involves the condensation of acetoacetic acid and 3-ethylthiobutyaldehyde, followed by Micheal addition with diethyl malonate, hydrolysis, and then decarboxylation. The economics of this route are poor from the standpoint of yield and the high cost of diethyl malonate. By contrast, the present invention gives good yields and obviates the need for this expensive reagent.

The following examples will further illustrate the invention.

EXAMPLE 1

Preparation of 4-Carboethoxy-5-[2-(ethylthio)-propyl]-1,3-cyclohexanedione

The unsaturated ester of the formula CH₃CH₂S(CH₃)CHCH₂CH=CHCOOCH₃ (1.0 g, 5.3 mmole) was added to a solution of ethyl acetoacetate (0.68 g, 5.3 mmole) and sodium metal (0.36 g, 16.9 mmole) in 20 mL of dry ethanol and heated to reflux for 18 hours. After cooling, the ethanol was evaporated and partitioned between H₂O and CH₂Cl₂. The aqueous product layer was acidified with HCl to pH=1 and extracted with CH₂Cl₂. This organic layer was dried over sodium sulfate and evaporated to give 0.88 g (57.8%) of product as a yellow oil which was partially crystalline. The target product was identified by IR and NMR.

EXAMPLE 2

5-[2-(Ethylthio)-propyl]-1,3-cyclohexanedione

The ester product of Example 1 (0.70 g, 2.4 mmole) was dissolved in 15 ml of methanol and 1 ml of 2N NaOH and heated to reflux for 2½ hours. The mixture was maintained at room temperature overnight. Methanol was evaporated, and the residue partitioned between about 30 ml of toluene and about 30 ml of aqueous HCl. The toluene extract was dried over sodium sulfate and evaporated to give 0.35 g (66.8%) of product as a yellow solid which was identical with an authentic sample. This target product was further identified by NMR.

The invention has been described in detail with particular reference to preferred embodiments thereof, but it will be understood that variations and modifications will be effected within the spirit and scope of the invention.

I claim:

1. The process for preparing a 4-carboalkoxy-5-[2-(alkylthio)-alkyl]-1,3-cyclohexanedione of the formula

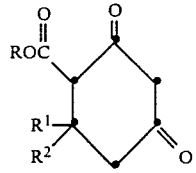

comprising reacting an acetoacetic ester of the formula R—OOCCH₂COCH₂ with an unsaturated ester of the formula R¹R²C=CHCOOR³ in the presence of ethanolic sodium ethoxide catalyst, wherein:

R is ethyl;
R¹ and R² are each selected independently from: H; alkyl; cycloalkyl; alkyl substituted cycloalkyl; aryl, aryl substituted with alkyl of 1–6 carbons, alkoxy or 1–6 carbons, or halogen; heterocyclic; or heterocyclic substituted with alkyl of 1–6 carbons, alkoxy of 1–6 carbons, or halogen; with the provision that at least one of R¹ and R² is an alkylthioalkyl group and wherein the alkyl groups or moieties of R¹ and R² are 1–18 carbons; and
R³ is alkyl of 1–6 carbons or cycloalkyl.

2. The process of claim 1 wherein the alkyl groups or moieties are 1–6 carbons.

3. The process of claim 1 wherein R is $CH_2CH_3$, $R^1$ is H, $R^2$ is $CH_3CH_2S(CH_3)CHCH_2-$, and $R^3$ is $CH_3$.

4. The process of claim 1 wherein the catalyst is sodium ethoxide, the molar ratio of sodium ethoxide to total moles of reactants is from about 0.10 to about 10.0, the molar ratio of acetoacetic ester to unsaturated ester is from about 0.8 to about 1.5, the weight rati of total reactants to ethanol is from about 0.01 to about 1.2, and the reaction temperature is from about 22° C. to about 78° C.

5. The process of claim 4 wherein the catalyst is sodium ethoxide, the molar ratio of sodium ethoxide to total moles of reactants is from about 1.0 to about 4.0, the molar ratio of acetoacetic ester to unsaturated ester is from about 1.0 to about 1.1, the weight ratio of total reactants to ethanol is from about 0.08 to about 1.0, and the reaction temperature is from about 70° C. to about 78° C.

* * * * *